United States Patent [19]
Tazaki et al.

[11] Patent Number: 5,264,627
[45] Date of Patent: Nov. 23, 1993

[54] METHOD FOR PRODUCTION OF METHACRYLIC ACID

[75] Inventors: Hiroyuki Tazaki; Ikuo Kurimoto, both of Himeji; Hiroyuki Uhara, Tatsuno; Yukio Aoki, Ibo, all of Japan

[73] Assignee: Nippon Shokubai Co., Ltd., Osaka, Japan

[21] Appl. No.: 909,649

[22] Filed: Jul. 7, 1992

[30] Foreign Application Priority Data

Jul. 9, 1991 [JP] Japan .................................. 3-168481

[51] Int. Cl.$^5$ ................................................ C07C 51/00
[52] U.S. Cl. ........................................................ 562/599
[58] Field of Search ............................................ 562/599

[56] References Cited

U.S. PATENT DOCUMENTS

| | | | |
|---|---|---|---|
| 4,374,270 | 2/1983 | Ruszola et al. | 562/599 |
| 4,954,650 | 9/1990 | Abe et al. | 562/534 |
| 5,206,431 | 4/1993 | Hashiba et al. | 562/534 |

FOREIGN PATENT DOCUMENTS

| | | |
|---|---|---|
| 418657 | 3/1991 | European Pat. Off. . |
| 0441312 | 8/1991 | European Pat. Off. . |
| 0450596 | 10/1991 | European Pat. Off. . |
| 61-221149 | 3/1985 | Japan . |

*Primary Examiner*—Paul J. Killos
*Attorney, Agent, or Firm*—Omri M. Behr; Matthew J. McDonald

[57] ABSTRACT

A method for the production of methacrylic acid comprising the steps of simultaneously introducing at least one compound selected from the group consisting of methacrolein and isobutyl aldehyde and a molecular oxygen-containing gas into a heat exchanger type shell-and-tube reaction vessel packed with an oxide catalyst containing molybdenum and phosphorus thereby effecting catalytic vapor-phase oxidation reaction and/or catalytic vapor-phase oxidative dehydrogenation reaction and consequently forming methacrylic acid, which method is characterized by having the empty space in the gas outlet part of said reaction vessel with a solid filler.

9 Claims, No Drawings

METHOD FOR PRODUCTION OF METHACRYLIC ACID

BACKGROUND OF THE INVENTION

1. Field of the Invention

This invention relates to a method for the production of methacrylic acid. More particularly, it relates to a method for producing methacrylic acid by subjecting at least one compound selected from the group consisting of methacrolein and isobutyl aldehyde or at least one compound selected from the group consisting of isobutylene, t-butanol, and methyl-t-butyl ether to catalytic vapor-phase oxidation using a molecular oxygen-containing gas.

2. Description of the Prior Art

Heretofore, for the production of methacrylic acid by catalytic vapor-phase oxidation of isobutylene, t-butanol, or methyl-t-butyl ether, the so-called two-stage oxidation reaction which comprises provisionally converting isobutylene, t-butanol, or methyl-t-butyl ether into methacrolein by catalytic vapor-phase oxidation in the presence of a catalyst (this reaction and the catalyst used therein will be occasionally referred to hereinafter as "former-stage reaction" and "former-stage catalyst" respectively) and subsequently converting methacrolein into methacrylic acid by catalytic vapor-phase oxidation in the presence of a catalyst (this reaction and the catalyst used therein will be occasionally referred to hereinafter as "latter-stage reaction" and "latter-stage catalyst" respectively) has been generally adopted. The oxide catalyst containing bismuth, molybdenum, and iron has been generally used as the former-stage catalyst and the oxide catalyst containing molybdenum and phosphorus as the latter-stage catalyst respectively in the two-stage reaction.

The method of producing methacrylic acid by subjecting isobutyl aldehyde to catalytic vapor-phase oxidative dehydrogenation and oxidation in the presence of the latter-stage catalyst has been also adopted.

The methacrylic acid which is produced as described above is generally subjected to a purifying treatment and then commercially utilized as a raw material for the production of an alkyl methacrylate by the reaction of esterification with an alcohol of 1 to 12 carbon atoms, for example. The alkyl methacrylate which is thus produced is commercially utilized as a raw material for the production of a polyalkyl methacrylate by homopolymerization or copolymerization with an other monomer.

The alkyl methacrylate produced by using as the raw material the methacrylic acid obtained by the conventional method described above, however, contains impurities in a minute amount. In all these impurities, the furan type compounds are considered to form one cause for the coloration of the polyalkyl methacrylate which is obtained by the polymerization of the alkyl methacrylate.

Particularly in the case of polymethyl methacrylate as a general-purpose polymer among other polyalkyl methacrylates, the coloration due to the presence of the furan compounds occurs to a large degree. By this reason, various measures are taken to enhance the transparency of the polymethyl methacrylate by removing such furan compounds.

The furan compounds which are contained as impurities in the methyl methacrylate are considered to originate from trace of impurities, particularly diketones, contained in the methacrylic acid as the raw material. For the purpose of decreasing the content of furan compounds in the methyl methacrylate, therefore, not only the decrease of the content of furan compounds in methyl methacrylate by the purifying treatment but also the decrease of the content of diketones in the methacrylic acid as the raw material is an indispensable requirement. Heretofore, for the purpose of decreasing the content of diketones in the aqueous methacrylic acid solution obtained from the methacrylic acid absorption column, methods of increasing the ratio of extraction of diketones as by varying the kind of the solvent to be used in the step of solvent extraction which is one of the steps for purification have been adopted.

According to our knowledge, while the gas containing methacrolein and/or methacrylic acid contains some ten to some hundred mol ppm, occasionally some thousand mol ppm, of diketones, based on the amount of the compound as raw material, the aqueous methacrylic acid solution obtained from the methacrylic acid absorption column still contains some ten to some hundred mol ppm of diketones based on the amount of methacrylic acid even after extraction from the solvent. As already described, the diketones form a cause for the formation of the furan type compounds. For the purpose of repressing the content of furan compounds in the ester such as methyl methacrylate to some ten mol ppm, it is necessary that the content of diketones in methacrylic acid should be also repressed to some ten mol ppm. Under the present condition, the relevant reaction products are in need of further purification.

When the number of steps of purification is increased, however, a serious economic disadvantage arises in respect that the loss of methacrylic acid is increased, the utility involved in purification is increased, and the cost of production of methacrylic acid or the ester thereof is proportionately boosted.

Further, in the production of methacrylic acid, when the content of diketones in methacrylic acid is increased by aging or by a change in the reaction condition of the step of oxidation, for example, the sole operation of removing impurities in the step of purification does not deserve to be called sufficient and, therefore, calls for an additional measure to decrease the content of diketones.

An object of this invention is to provide a novel method for the production of methacrylic acid.

Another object of this invention is to provide a method for very simple and inexpensive production of methacrylic acid, which method curbs formation of diketones as by-products and allows production of methacrylic acid having an extremely small content of diketones and enjoying high quality.

SUMMARY OF THE INVENTION

These objects are accomplished by a method for producing methacrylic acid by simultaneously introducing at least one compound selected from the group consisting of methacrolein and isobutyl- aldehyde and a molecular oxygen-containing gas into a heat exchanger type shell-and-tube reaction vessel packed with an oxide catalyst containing molybdenum and phosphorus thereby effecting catalytic vapor-phase oxidation reaction and/or catalytic vapor-phase oxidative dehydrogenation reaction, which method is characterized by having an empty space of a gas outlet of the reaction vessel packed with a solid packing.

The objects are further accomplished by a method for producing methacrylic acid by simultaneously introducing at least one compound selected from the group consisting of isobutylene, t-butanol, and methyl-t-butyl ether and a molecular oxygen-containing gas into a first heat exchanger type shell-and-tube reaction vessel packed with an oxide catalyst containing bismuth, molybdenum, and iron thereby effecting catalytic vapor-phase oxidation reaction and consequent formation mainly of methacrolein and subsequently simultaneously introducing the resultant methacrolein-containing gaseous reaction product and a molecular oxygen-containing gas into a second heat exchanger type shell-and-tube reaction vessel packed with an oxide catalyst containing molybdenum and phosphorus thereby effecting catalytic vapor-phase oxidation reaction and consequent formation of methacrylic acid, which method is characterized by having an empty space of a gas outlet of the second reaction vessel packed with a solid packing.

In the case of this method, the empty space in the gas outlet of the first reaction vessel may be packed with a solid packing when necessary.

We have continued various studies in search of a way of attaining these objects. As a result, we have experimentally confirmed the following fact and perfected this invention.

Specifically, for the purpose of decreasing the content of diketones, it is necessary that not only the aqueous methacrylic acid solution should be subjected to a purifying treatment but also the diketones occurring should be decreased or the formation of the diketones should be curved during the stage of production of a gas containing methacrolein and/or methacrylic acid. The method which fulfills this requirement is highly advantageous economically because it obviates the necessity for enhancing the capacity for purification.

For the purpose of elucidating the mechanism responsible for the formation of diketones, we conducted an experiment on passage through an empty cylinder kept at temperatures above 310° C., the temperature for the formation of methacrylic acid, of a methacrolein and methacrylic acid containing gas resulting from the catalytic vapor-phase oxidation reaction of isobutylene, t-butanol, or methyl-t-butyl ether and methacrylic acid containing gas resulting from the catalytic vapor-phase oxidation reaction and/or the catalytic vapor-phase oxidative dehydrogenation reaction of methacrolein or isobutyl aldehyde, to find that the gas showed an increase in the content of diketones and the increase of this content tended to grow in proportion as the retention time of the gas within the empty cylinder increased. These results of the experiment clearly indicate that the diketones are not only formed in the catalyst bed but also formed sequentially in the empty space which follows the gas outlet of the reaction vessel.

Though the experiment has not completely elucidated the mechanism responsible for the formation of diketones, it has yielded the results admitting an inference that various unstable substances, for example aldehydes such as methacrolein, acrolein, and acetaldehyde, and ketones represented by acetone which occur in the gas containing methacrolein and/or methacrylic acid are converted probably by thermal decomposition into diketones when the gas is retained for some time in an empty space kept at temperatures exceeding a certain level.

In any event, the diketones are sequentially formed from the gas containing methacrolein and/or methacrylic acid as the gas remains for some time within the empty space kept at the temperatures exceeding the fixed level. We have concluded that for the purpose of curbing the formation of diketones, the inner volume of the empty space in the gas outlet of the reaction vessel must be decreased.

When a solid filler was placed to fill the empty space in the gas outlet of the reaction vessel and tried to decrease the inner volume of the empty space, it was confirmed to be highly effective in curbing the sequential formation of diketones.

In accordance with the method of this invention for the production of methacrylic acid, since a solid packing placed to fill the empty space of the gas outlet of the reaction vessel serves the purpose of decreasing the inner volume of the empty space and consequently repressing the sequential formation of diketones in the empty space of the gas outlet, the occurrence of diketones as by-products can be curbed and the production of a methacrylic acid-containing gas having an extremely small content of diketones can be attained by a very simple and inexpensive procedure. As a result, the loss of methacrylic acid during the step for purification of methacrylic acid can be decreased, the yield of methacrylic acid can be substantially increased, and the production of methacrylic acid having an extremely small content of diketones and enjoying high quality can be obtained. This method is incapable of either causing conversion of the produced methacrylic acid to any other compound or suffering compounds formed from diketones by one treatment or other to affect adversely the quality of the produced methacrylic acid.

DESCRIPTION OF THE PREFERRED EMBODIMENTS

The method of this invention for the production of methacrylic acid comprises simultaneously introducing at least one compound selected from the group consisting of methacrolein and isobutyl aldehyde and a molecular oxygen-containing gas into a heat exchanger type shell-and-tube reaction vessel packed with an oxide catalyst containing molybdenum and phosphorus thereby effecting catalytic vapor-phase oxidation reaction and/or catalytic vapor-phase oxidative dehydrogenation reaction and consequently forming methacrylic acid, which method is characterized by having the empty space in the gas outlet of the reaction vessel packed with a solid packing.

The method of this invention for the production of methacrylic acid comprises simultaneously introducing at least one compound selected from the group consisting of isobutylene, t-butanol, and methyl-t-butyl ether and a molecular oxygen-containing gas into a first heat exchanger type shell-and-tube reaction vessel packed with an oxide catalyst containing bismuth, molybdenum, and iron thereby effecting catalytic vapor-phase oxidation reaction and consequently forming methacrolein mainly and subsequently simultaneously introducing the resultant methacrolein-containing gaseous reaction product and a molecular oxygen-containing gas into a second heat exchanger type shell-and-tube type reaction vessel packed with an oxide catalyst containing molybdenum and phosphorus thereby effecting catalytic vapor-phase oxidation reaction and consequently forming methacrylic acid, which method is characterized by having the empty space in the gas outlet of the second reaction vessel packed with a solid packing.

In the case of this method, the empty space in the gas outlet of the first reaction vessel may be packed with a solid packing when necessary.

The empty space in the gas outlet of the reaction vessel which is packed with the solid packing as contemplated by this invention embraces the empty space which remains in the catalyst tube after the tube has been packed with the catalyst, the empty space which occurs in the crown part of the reaction vessel, and the empty space in the reaction gas outlet conduit connected to the crown part. Though the idea of using a catalyst tube packed with an inactive carrier of a ceramic substance has been known to the art, the method of this invention which has originated in the special interest taken in the aforementioned behavior of diketones manifested in the empty space of the outlet of the crown part of the reaction vessel and which resides in packing the empty space with a filler and consequently decreasing the inner volume of this empty space has never existed to date.

Though the solid filler to be used in this invention is not specifically defined, the following materials (1) to (5) may be suitably used either singly or in the form of a mixture of two or more members.

(1) Oxides containing bismuth and molybdenum elements as essential components.

(2) Oxides containing phosphorus and molybdenum elements as essential components.

(3) Refractory inorganic materials such as alpha-alumina, silica, silica-alumina, zirconia, magnesia, titania, silicon carbide, silicon nitride, and tin oxide.

(4) Metallic materials such as stainless steel, iron, aluminum, and titanium.

(5) Refractory inorganic materials or metallic material having the surface treated with acidic compounds.

The shape of the solid packing is not specifically defined. The shapes which are generally adopted for catalyst carriers and packing such as, for example, pellets, beads, rings, honeycombs, spheres, plates, spirals, fibers, and meshes fit for demisters can be cited as examples of the shape usable effectively for the solid filler of this invention.

As regards the shape of the solid packing for use in this invention, the rodlike solid packing may be in the form of a straight bar, a zigzag bar, a spiral bar, a polygonal prism, or a circular column, for example, and the platelike insert in the form of a ribbon, a zigzag plate, or a spiral plate, for example. The platelike insert need not be in the form of a perfect plate but may be in the form of a reticular plate. As regards the size of the insert, the overall length is desired to be in the range of 200 to 1,000 mm, preferably 250 to 500 mm and the width is desired to be such that the void ratio may fall in the following range.

Though the void ratio of the empty space of the gas outlet of the former-stage or latter-stage catalyst bed packed with the solid packing is suitably selected depending on the particular shape of the filler to be used, it is preferable to be in the range between 30 and 99.9% by volume, preferably between 33 and 99.9 % by volume. The reason for this range is that the formation of diketones in the filler bed can be effectively curbed and the decomposition of diketones therein can be effectively carried out when the void ratio is adjusted within this range.

The term "void ratio" as used in this invention refers to what is defined by the following formula.

Void ratio (%) = {(Inner volume of empty space — volume of filler)/inner volume of empty space} × 100

The effect which is manifested by the packing of the solid packing in curbing the formation of diketones as contemplated by this invention is considered to be ascribable, as already described, to the decrease in the inner volume of the empty space in the gas outlet of the reaction vessel. In consideration of this fact coupled with the fact that, as specifically demonstrated in Example 8 to be cited hereinbelow, such a packing as a demister which is not thought to be very effective in decreasing the inner volume of the empty space exhibits a surprising effect in curbing the formation of diketones, it is safe to infer that the curbing of the formation of diketones is additionally ascribable to the extinction of radicals formed in the empty cylinder due to collision thereof with the solid packing and the local increase in linear velocity of the gas flow due to disturbance thereof caused the solid packing.

Since the temperature of the filler bed is allowed to remain in the range between 200° and 380° C., the gas produced by the reaction can be introduced in its unaltered form into the packing layer. The retention time for the gas in the empty space of the gas outlet packed with the filler is preferable to be in the range between 0.1 and 30 seconds, especially between 0.5 and 20 seconds.

Though the method itself of producing methacrylic acid aimed at by this invention is not specifically defined, the production may be accomplished by immediately bringing the raw material gas containing methacrolein and isobutyl aldehyde into contact with the latter-stage catalyst thereby effecting vapor-phase oxidation reaction and/or vapor-phase oxidative dehydrogenation reaction, for example. To be specific, the method is desired to be carried out as follows.

A raw material gas containing 1 to 10% by volume of at least one compound selected from the group consisting of isobutylene, t-butanol, and methyl-t-butyl ether, 3 to 20% by volume of molecular oxygen, 0 to 60% by volume of steam, and such inactive gases as nitrogen and carbon dioxide is supplied at a temperature (catalyst temperature in the reaction vessel) in the range between 250° and 450° C., preferably between 280° and 420° C., at a space velocity in the range between 300 and 5,000 hr$^{-1}$, preferably between 500 and 4,000 hr$^{-1}$, (STP) into a first heat exchanger type shell-and-tube reaction vessel packed with a bismuth-molybdenum-iron-containing multi-component oxide catalyst (former-stage catalyst) intended mainly for formation of methacrolein and optionally having a solid packing packed in the empty space of the crown part of the outlet for the gaseous reaction product for the purpose of curbing the occurrence of diketones as by-products to effect former-stage reaction and produce a methacrolein-containing gas.

Then, a mixed gas prepared by adding secondary air, secondary oxygen, or steam, when required, to the methacrolein-containing gas obtained in the former-stage reaction is supplied at a temperature (catalyst temperature in the reaction vessel) in the range between 100° and 380° C., preferably between 150° and 350° C., at a space velocity in the range between 300 and 5,000 hr$^{-1}$, preferably between 500 and 4,000 hr$^{-1}$, (STP) into a second heat exchange type shell-and-tube reaction vessel packed with an oxide catalyst containing molybdenum and phosphorus (latter-stage catalyst) intended for formation of methacrylic acid and optionally having a solid packing packed in the empty space of the crown part of the outlet for the gaseous reaction product for the purpose of curbing the occurrence of diketones as by-products to effect latter-stage reaction and produce methacrylic acid.

The catalyst to be used in the former-step reaction is at least one oxide catalyst having bismuth, iron, and molybdenum as its main components. The catalyst of the following composition proves particularly preferable.

$$Mo_a W_b Bi_c Fe_d A_e B_f C_g D_h O_x$$

wherein Mo stands for molybdenum, W for tungsten, Bi for bismuth, Fe for iron, A for at least one element selected from the group consisting of nickel and cobalt, B for at least one element selected from the group consisting of alkali metals, alkaline earth metals, and thallium, C for at least one element selected from the group consisting of phosphorus, tellurium, antimony, tin, cerium, lead, niobium, manganese, and zinc, D for at least one element selected from the group consisting of silicon, aluminum, titanium, and zirconium, and O for oxygen. Then, a, b, c, d, e, f, g, h, and x respectively stand for the numbers of atoms of the elements of Mo, W, Bi, Fe, A, B, C, D, and O such that, where a is assumed to be 12, b is in the range of 0 to 10, c in the range of 0.1 to 10, d in the range of 0.1 to 20, e in the range of 2 to 20, f in the range of 0 to 10, g in the range of 0 to 4, h in the range of 0 to 30, and x assumes a numerical value to be fixed by the states of oxidation of the elements.

The former-step catalyst may be in the form of pellets produced by the use of a tableting machine or an extrusion molder, for example, in the form of beads, or in the form of rings containing a through hole. It may be effectively used in the form of a composite having a catalytic substance deposited on a refractory carrier.

The latter-step catalyst is only required to be an oxide catalyst containing molybdenum and phosphorus as main components. It is preferable to contain a phosphomolybdic acid type heteropolyacid or a metal salt thereof. The catalyst of the following composition proves particularly preferable.

$$Mo_a P_b A_c B_d C_e D_f O_x$$

wherein Mo stands for molybdenum, P for phosphorus, A for at least on element selected from the group consisting of arsenic, antimony, germanium, bismuth, zirconium, and selenium, B for at least one element selected from the group consisting of copper, iron, chromium, nickel, manganese, cobalt, tin, silver, zinc, palladium, rhodium, and tellurium, C for at least one element selected from the group consisting of vanadium, tungsten, and niobium, D for at least one element selected from the group consisting of alkali metals, alkaline earth metals, and thallium, and O for oxygen. Then, a, b, c, d, e, f, and x respectively stand for the atomic ratio of Mo, P, A, B, C, D, and O such that, where a is assumed to be 12, b is in the range of 0.5 to 4, c in the range of 0 to 5, d in the range of 0 to 3, e in the range of 0 to 4, f in the range of 0.01 to 4, and x assumes a numerical value to be fixed by the states of oxidation of the component elements.

The form in which the catalyst is used is not critical. This catalyst may be in the form of cylinders, in the form of hollow spheres, or in the form of beads. Of course, this catalyst may be used in the form of a composite having a catalytic substance deposited on a refractory carrier.

When methacrylic acid is produced using isobutylaldehyde as a reaction raw material, a reaction may be carried out under a similar reaction condition using a similar reactor to one used in oxidation of methacrolein, the latter-step catalyst and a solid packing.

Now, the present invention will be described more specifically hereinafter with reference to working examples, but is not limited by these examples.

EXAMPLES 1–10

Preparation of Former-Step Catalyst

Separately, 7.0 kg of cobalt nitrate was dissolved in 2 liters of distilled water, 2.4 kg of ferric nitrate and 0.6 liter of concentrated nitric acid in 2 liters of distilled water, and 2.9 kg of bismuth nitrate in 3 liters of distilled water acidified to prepare three nitrate solutions. Separately, 9.5 kg of ammonium paramolybdate and 4.9 kg of ammonium paratungstate were dissolved in 15 liters of water under heating and stirring, and a liquid obtained by dissolving 2.4 kg of 20% silica sol and 76 g of sodium nitrate in 1.5 liters of distilled water was added to the mixed aqueous solution obtained as described above. The suspension consequently produced was heated and stirred for evaporation. The resultant residue of evaporation was molded and then calcined under a current of air at 450° C. for six hours to prepare a catalyst. The metal composition of this catalyst in atomic ratio was as follows.

$$Co_4 Fe_1 Bi_1 W_3 Mo_9 Si_{1.35} Na_{0.1}$$

Preparation of Latter-Step Catalyst

In 40 liters of heated water, 17.7 kg of ammonium paramolybdate and 1.9 kg of ammonium metavanadate were stirred and dissolved. To the resultant solution, 4 kg of pyridine and 1.25 kg of phosphoric acid (85% by weight) were added and then a mixed solution obtained by dissolving 11 kg of nitric acid, 1.8 kg of strontium nitrate, 2.5 kg of calcium nitrate, and 0.4 kg of copper nitrate in 220 liters of water was added. The resultant mixture was stirred and heated to be concentrated. The clayish substance consequently obtained was molded in a cylindrical form of 5 mm $\phi \times$ 5 mm L ($\phi$: diameter, L; long), dried at 250° C., and calcined under a current of nitrogen at 450° C. for four hours and under a current of air at 400° C. for two hours. Consequently, there was obtained a catalyst oxide. The composition of this catalyst except for oxygen in atomic ratio was as follows.

$$P_{1.3} Mo_{12} V_2 Sr_{1.0} Ca_{1.5} Cu_{0.2}$$

Method of Reaction

In a reactor formed of 24 stainless steel reaction tubes 25.4 mm in inside diameter and 5,000 mm in length and adapted to effect exchange of heat through circulation of molten salt, the aforementioned former-step catalyst was packed in the form of a bed 1,700 mm in height and heated to 340° C.

In a separate reactor formed of 24 stainless steel reaction tubes 25.0 mm in inside diameter and 4,000 mm in length and adapted to effect exchange of heat through circulation of molten salt, the aforementioned latter-step catalyst was packed in the form of a bed 3,200 mm in height and heated to 310° C.

The two reactors thus prepared were interconnected with a conduit provided with nozzles for introduction of a molecular oxygen-containing gas and steam and further provided with a heat-exchanger, so as to permit introduction of the gas formed by the reaction in the reactor containing the former-step catalyst into the reactor containing the latter-step catalyst.

Through the gas inlet part of the former-step catalyst bed, a mixed gas consisting of 6.0% by volume of isobutylene, 13.2% by volume of oxygen, 10.0% by volume of steam, and the balance of nitrogen gas was supplied to the former-step catalyst at a space velocity of 1,600 hr$^{-1}$ (STP).

Then, at the inlet to the latter-step catalyst bed, the feed gas was replenished with secondary air in such an amount as to adjust the molar ratio of oxygen ($O_2$) to methacrolein (MAL), $O_2$/MAL, to 2.5.

The empty space extending from the lower part of the catalyst bed in the latter-stage reaction vessel (the outlet for the reaction gas) to the crown part of the reaction vessel was packed with a varying solid packing indicated in Table 1 at a void ratio similarly indicated in the table. The raw material gas was passed with a retention time of 7 seconds through the reaction vessel kept at 310° C.

The reaction gas emanating from the reaction vessel was collected as condensed and assayed for acetonylacetone, one species of diketone. The results are shown in Table 1.

In a blank test having absolutely no solid filler placed in the empty space of the gas outlet of the latter-stable reaction vessel, the gas emanating from the outlet of the catalyst bed was found to have 38 mol ppm of acetonylacetone formed based on the amount of isobutylene in the feed gas. The gas emanating from the empty space of the outlet of the latter-stage reaction vessel was found to contain 297 mol ppm of acetonylacetone based on the amount of isobutylene in the feed gas. In the samples of the blank test and the present test, the conversion of isobutylene was 99.0 mol% and the per-pass yield of methacrylic acid was 68.5 mol% invariably, indicating absence of any discernible decrease in the yield of methacrylic acid. This fact allows a logical inference that the sequential reaction of methacrylic acid in the solid filler bed can be disregarded.

TABLE 1

| Example | Solid packing | Void ratio (%) | Amount of acetonylacetone at outlet of solid packing bed (mol ppm)* |
|---|---|---|---|
| Example 1 | Bismuth-molybdenum type oxide (rings 10 mm in outside diameter, 10 mm in length, and 6 mm in through hole diameter | 58 | 49 |
| Example 2 | Phosphorus-molybdenum type oxide (rings 10 mm in outside diameter, 10 mm in length, and 6 mm in through hole diameter | 55 | 47 |
| Example 3 | Silicon carbide type (rings 10 mm in outside diameter, 10 mm in length, and 6 mm in through hole diameter | 59 | 51 |
| Example 4 | Alpha-alumina (pellets 10 mm in outside diameter and 10 mm in length) | 33 | 57 |
| Example 5 | Silica-alumina (spheres 10 mm in outside diameter | 34 | 49 |
| Example 6 | Porcelain Rasching rings (10 mm in outside diameter, 8 mm in length, and 7 mm in through hole diameter) | 52 | 60 |
| Example 7 | Rasching rings of stainless steel (10 mm in outside diameter, 8 mm length, and 9.2 mm in through hole diameter) | 86 | 68 |
| Example 8 | Demister of stainless steel (40 kg/m$^3$ of density) | 99.5 | 70 |
| Example 9 | Metal plate made of SUS 304 having 30 mm of length wherein the plate having 0.4 mm of thickness and 17 mm of width is folded in zigzag shape at about 90° and 35 mm of pitch between top and top | 99.5 | 75 |
| Example 10 | Insert having structure at 17 mm of width and 45 mm of pitch of the same material of Example 4. | 99.5 | 75 |

*Amount formed, based on the amount of isobutylene supplied.

EXAMPLES 11 TO 20

Production of methacrylic acid was carried out by repeating the procedures of Examples 1 to 10, except that the same solid packings used in Examples 1 to 10 were placed in the same void ratios severally in the empty space extending from the outlet of the catalyst bed in the former-stage reaction vessel to the crown part of the reaction vessel and the gaseous reaction product from the former-stage reaction was passed with a retention time of 9 seconds through the reaction vessel.

In the blank test, the reaction gas emanating from the former-stage reaction vessel was found to contain 472 mol ppm based on the amount of isobutylene fed to the reaction.

The results of the reaction are shown in Table 2. In this table, the amount of acetonylacetone A represents the value found of the gas which had passed the solid packing in the outlet of the former-stage reaction vessel and the amount of acetonylacone B the value found of the gas which had passed the solid packing in the latter-stage reaction vessel.

TABLE 2

| Example | Amount of acetonylacetone A (mol ppm)* | Amount of acetonylacetone B (mol ppm)* |
|---|---|---|
| Example 11 | 77 | 47 |
| Example 12 | 74 | 47 |
| Example 13 | 87 | 50 |
| Example 14 | 90 | 55 |
| Example 15 | 79 | 46 |
| Example 16 | 92 | 56 |
| Example 17 | 103 | 66 |
| Example 18 | 107 | 70 |
| Example 19 | 110 | 76 |
| Example 20 | 110 | 76 |

*Amount formed, based on the amount of isobutylene supplied.

EXAMPLE 21

Methacrylic acid was produced in the presence of a catalyst containing phosphorus and molybdenum (latter-stage catalyst) by following the procedure of Example 1, except that the use of the former-stage reaction vessel was omitted and isobutyl aldehyde was used as the raw material for reaction in the place of methacrolein and this raw material was introduced to the inlet of the latter-stage reaction vessel. In the blank test, the gas emanating from the reaction vessel was found to contain 253 mol ppm of acetonylacetone based on the amount of isobutyl aldehyde used as the raw material. When a bismuth-molybdenum type oxide was used instead as a solid packing, the gas emanating from the solid filler bed was found to contain 42 mol ppm of acetonylacetone based on the amount of isobutyl aldehyde fed to the reaction.

EXAMPLE 22

Methacrylic acid was produced by following the procedure of Example 1, except that t-butanol was used as the raw material in the place of isobutylene. In the blank test, the gas emanating from the reaction vessel was found to contain 295 mol ppm of acetonylacetone based on the amount of the raw material fed to the reaction. When a bismuth-molybdenum type oxide was used instead as the solid filler, the amount of acetonylacetone contained in the reaction gas emanating from the solid filler bed was 48 mol ppm based on the amount of the raw material fed to the reaction.

EXAMPLE 23

Methacrylic acid was produced by following the procedure of Example 1, except that methyl-t-butyl ether was used as the raw material in the place of isobutylene. In the blank test, the gas from the reaction was found to contain 283 mol ppm of acetonylacetone based on the amount of the raw material fed to the reaction. When a bismuth-molybdenum type oxide was used instead as a solid packing, the reaction gas emanating from the solid packing bed was found to contain 47 mol ppm of acetonylacetone based on the amount of the raw material fed to the reaction.

EXAMPLE 24

Methacrylic acid was produced by following the procedure of Example 1, except that the same solid packing as used in Example 1 was placed in a void ratio of 58% in the empty space extending from the outlet of the catalyst bed in the former-stage reaction vessel to the crown part of the former-stage reaction vessel and t-butanol was used as the raw material for the reaction in the place of isobutylene.

In the blank test, the gas emanating from the former-stage reaction vessel was found to contain 463 mol ppm of acetonylacetone based on the amount of the raw material fed to the reaction. When the solid filler was placed in the outlet parts of both the former-stage and latter-stage reaction vessels, the gas emanating from the outlet of the former-stage reaction vessel was found to contain 40 mol ppm of acetonylacetone and the gas from the outlet of the latter-stage reaction vessel 50 mol ppm, respectively based on the amount of the raw material fed to the reaction.

EXAMPLE 25

Methacrylic acid was produced by following the procedure of Example 1, except that the same solid packing as used in Example 1 was placed in a void ratio of 58% in the empty space extending from the outlet of the catalyst bed in the former-stage reaction vessel to the crown part of the former-stage reaction vessel and methyl-t-butyl ether was used instead as the raw material in the place of isobutylene.

In the blank test, the gas emanating from the outlet of the former-stage reaction vessel was found to contain 447 mol ppm of acetonylacetone based on the amount of the raw material fed to the reaction. When the solid packing was placed in the outlet part of both the former-stage and latter-stage reaction vessels, the gas emanating from the former-stage reaction vessel was found to contain 39 mol ppm of acetonylacetone and the gas from the latter-stage reaction vessel 45 mol ppm of acetonylacetone, respectively based on the amount of the raw material fed to the reaction.

What is claimed is:

1. A method for the production of methacrylic acid comprising the steps of simultaneously introducing at least one compound selected from the group consisting of methacrolein and isobutyl aldehyde and a molecular oxygen-containing gas into a heat exchanger type shell-and-tube reaction vessel packed with an oxide catalyst containing molybdenum and phosphorus thereby effecting catalytic vapor-phase oxidation reaction and/or catalytic vapor-phase oxidative dehydrogenation reaction and consequently forming methacrylic acid, which method is characterized by having the empty space in the gas outlet part of said reaction vessel with a solid packing.

2. A method according to claim 1, wherein the void ratio in the empty space of the gas outlet part packed with said solid filler is in the range between 30 and 99.9% by volume.

3. A method according to claim 1 or claim 2, wherein said solid packing consists of lumps of a metal oxide, a refractory inorganic material, or metallic material.

4. A method according to claim 3, wherein said solid filler is formed in the shape of pellets, beads, rings, honeycombs, sheres, plates, spirals, fibers, or meshes.

5. A method for the production of methacrylic acid comprising the steps of simultaneously introducing at least one compound selected from the group consisting of isobutylene, t-butanol, and methyl-t-butyl ether and a molecular oxygen-containing gas into a first heat exchange type shell-and-tube reaction vessel packed with an oxide catalyst containing bismuth, molybdenum, and iron thereby effecting catalytic vapor-phase oxidation reaction and consequently forming methacrolein mainly, then simultaneously introducing *,he resultant methacrolein-containing gaseous reaction product and a molecular oxygen-containing gas into a second heat exchange type shell-and-tube reaction vessel thereby effecting catalytic vapor-phase oxidation reaction and consequently forming methacrylic acid, which method is characterized by having the empty space of the gas outlet of said second reaction vessel packed with a solid packing.

6. A method according to claim 5, wherein the empty space in the gas outlet of said first reaction vessel is packed with said solid packing.

7. A method according to claim 5, wherein the void ratio in the empty space of the gas outlet packed with said solid packing is in the range between 30 and 99.9% by volume.

8. A method according to claim 5 or claim 7, wherein said solid packing consists of lumps of a metal oxide, a refractory inorganic material, or metallic material.

9. A method according to claim 8, wherein said solid filler is formed in the shape of pellets, beads, rings, honeycombs, spheres, plates, spirals, fibers, or meshes.

* * * * *